United States Patent
Kruger et al.

(10) Patent No.: US 9,208,561 B2
(45) Date of Patent: Dec. 8, 2015

(54) REGISTRATION METHOD AND REGISTRATION DEVICE FOR A POSITION DETECTION SYSTEM

(71) Applicant: Fiagon GmbH, Hennigsdorf (DE)

(72) Inventors: Timo Kruger, Berlin (DE); Dirk Mucha, Berlin (DE); Andreas Rose, Berlin (DE)

(73) Assignee: FIAGON GMBH, Hennigsdorf (DE)

( * ) Notice: Subject to any disclaimer, the term of this patent is extended or adjusted under 35 U.S.C. 154(b) by 0 days.

(21) Appl. No.: 14/401,652

(22) PCT Filed: May 17, 2013

(86) PCT No.: PCT/EP2013/060299
§ 371 (c)(1),
(2) Date: Nov. 17, 2014

(87) PCT Pub. No.: WO2013/171338
PCT Pub. Date: Nov. 21, 2013

(65) Prior Publication Data
US 2015/0170366 A1     Jun. 18, 2015

(30) Foreign Application Priority Data
May 18, 2012   (DE) .......................... 10 2012 208 389

(51) Int. Cl.
*G06K 9/00*      (2006.01)
*G06T 7/00*      (2006.01)
(Continued)

(52) U.S. Cl.
CPC .............. *G06T 7/0024* (2013.01); *G01C 11/06* (2013.01); *G06K 9/00624* (2013.01);
(Continued)

(58) Field of Classification Search
USPC ......... 382/100, 103, 128–134, 155, 162, 168,
382/173, 181, 189, 199, 209, 220, 232,
382/254–255, 274–276, 287–294, 305, 312,
382/321; 600/476, 407; 378/4, 21; 606/89,
606/91, 86 R, 1
See application file for complete search history.

(56) References Cited

U.S. PATENT DOCUMENTS

2004/0230199 A1* 11/2004 Jansen .................... A61B 5/064
606/91
2005/0119639 A1* 6/2005 McCombs ............. A61B 19/52
606/1
(Continued)

FOREIGN PATENT DOCUMENTS

| DE | 10 2009 030731 A1 | 12/2010 |
|---|---|---|
| WO | 2011/134083 A1 | 11/2011 |
| WO | 2012/056034 A1 | 5/2012 |

*Primary Examiner* — Seyed Azarian
(74) *Attorney, Agent, or Firm* — Ware, Fressola, Maguire & Barber LLP

(57) ABSTRACT

A registration method and device for detecting the position and alignment of an object or body part in relation to a position detection system, the method arranging a reference sensor on the object or body part and/or on an image sensor unit, detecting the position of the reference sensor by means of the position detection system, photogrammetrically detecting a surface of the object or body part by means of the image sensor unit, producing a surface model of the object or body part on the basis of the photogrammetrically detected information, determining the position of the reference sensor in the surface model, and correlating the surface model with a coordinate system of the position detection system on the basis of the determined position of the reference sensor in the surface model and on the basis of the position of the reference sensor detected by means of the position detection system.

19 Claims, 4 Drawing Sheets

(51) Int. Cl.
*G01C 11/06* (2006.01)
*A61F 2/46* (2006.01)
*A61B 19/00* (2006.01)
*G01C 3/08* (2006.01)

(52) U.S. Cl.
CPC ........ *A61B 19/5212* (2013.01); *A61B 19/5244* (2013.01); *A61B 2019/5251* (2013.01); *A61B 2019/5255* (2013.01); *A61B 2019/5263* (2013.01); *A61B 2019/5293* (2013.01); *A61B 2019/5295* (2013.01); *A61B 2019/5437* (2013.01); *A61B 2019/5495* (2013.01); *G01C 3/08* (2013.01); *G06T 2207/10012* (2013.01)

(56) References Cited

U.S. PATENT DOCUMENTS

| | | | | |
|---|---|---|---|---|
| 2008/0009697 | A1* | 1/2008 | Haider | A61B 17/14 600/407 |
| 2010/0312247 | A1* | 12/2010 | Tuma | A61B 17/1668 606/89 |
| 2011/0295329 | A1* | 12/2011 | Fitz | A61B 17/1739 606/86 R |
| 2013/0060146 | A1* | 3/2013 | Yang | G01B 11/245 600/476 |

\* cited by examiner

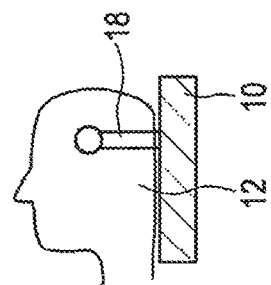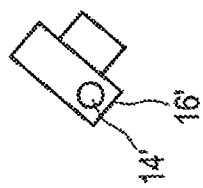
Fig. 2

REGISTRATION METHOD AND REGISTRATION DEVICE FOR A POSITION DETECTION SYSTEM

CROSS REFERENCE TO RELATED APPLICATIONS

This application is the U.S. National Stage of International Application Number PCT/EP2013/060299 filed on May 17, 2013 which application claims priority under 35 USC §119 to German Patent Application No. 10 2012 208 389.8 filed on Mar. 18, 2012, which applications are hereby incorporated by reference in their entirety.

TECHNICAL FIELD

The invention relates to a registration method for detecting the position and alignment of an object or body part in relation to a position detection system. The invention moreover relates to a device for performing such a method.

BACKGROUND OF THE INVENTION

Position detection systems which, for example in the medical field, support a navigation of instruments, for example surgical instruments, are known per se. Such position detection systems may be optical, ultrasound-based or electromagnetic position detection systems. Thus, for example, electromagnetic position detection systems are known, in which a field generator generates an alternating electromagnetic field and provision is made for position sensors comprising coils. Currents are induced into the coils by the alternating electromagnetic field from the generator, wherein said currents depend on the alignment of a respective coil in relation to the alternating electromagnetic field. If a movable instrument is aligned with such position sensors in the form of sensor coils, it is possible to determine place and location of the instrument relative to a reference sensor which, for example, may likewise comprise coils. In so doing, the reference sensor as a patient localizer is preferably fixedly connected to a body part of a patient for else a different object).

For the purposes of navigating in body parts of a patient, the position of an instrument is typically detected by means of such a position detection system and the position of the instrument is displayed in slice images of the body part obtained by tomography. In order for this to work, the position values supplied by the position sensor of the instrument must be transferred into coordinates of the tomographic image of the patient. By way of example, to this end, the practice of generating a topographic image of the surface of a body part from a tomographic image of a patient is known, in order to correlate points on the surface of the topographic image (also referred to as model surface below) with those points on the surface of the real body part which are respectively contacted by a pointer instrument or sensing instrument. Thus, a transformation prescription for transforming position values detected by means of the position detection system into model coordinates may be produced within the scope of a registration method. To this end, a plurality of points are sensed on the real surface of the body part and the associated position values, which of course represent points on a real surface, are correlated with points on the model surface while maintaining their relative position with respect to one another in such a way that this results in the smallest possible error. A transformation prescription specifying how detected position values are to be converted into coordinates of the topographic image—also referred to as topographic model here—and therefore also into coordinates of the tomographic image or model, emerges herefrom.

The patient registration refers to the establishment of a transformation function for bringing position data detected during the operation into correspondence with position information in image data obtained prior to surgery, for example by tomography. By way of example, for the purposes of patient registration, as described above, a patient model is detected and a transformation function is established which, within the scope of the registration method, brings detected position data and a patient model resulting therefrom into correspondence with position information relating to the image data obtained prior to surgery.

For the purposes of determining the transformation function, the same geometric features in the model and in the image data (for example obtained by tomography) are established in the respective coordinate system. The two coordinate systems are then correlated by means of these features. The surface registration by means of a pointer instrument is generally widespread. Here, the skin surface of the patient serves as corresponding feature. The skin surface is sensed by means of a pointer instrument during surgery and brought into correspondence with the extracted skin surface from the image data.

SUMMARY OF THE INVENTION

The invention is based on the object of specifying a registration method which can be performed as easily and quickly as possible.

According to the invention, this object is achieved by a registration method for detecting the position and alignment of an object or body part in relation to a position detection system, wherein the method comprises the following steps:
- arranging a reference sensor on the object or body part and/or on an image sensor unit,
- detecting the position of the reference sensor by means of the position detection system,
- photogrammetrically detecting a surface of the object or body part and optionally of the reference sensor by means of the image sensor unit,
- producing a surface model of the object or body part on the basis of the photogrammetrically detected information,
- determining the position of the reference sensor in the surface model, and
- correlating the surface model with a coordinate system of the position detection system on the basis of the determined position of the reference sensor in the surface model and on the basis of the position of the reference sensor detected by means of the position detection system.

An advantage offered by the registration method according to the invention is that it permits contactless registration and therefore avoids problems emerging in the case of known registration methods by means of a pointer instrument due to e.g. soft skin of a patient possibly deforming during contact with the pointer instrument. Moreover, since the optical registration allows a larger portion of the surface of a body part or object to be detected simultaneously, the registration can also be performed more quickly and, at the same time, more accurately.

Preferably, the photogrammetric detection of a surface of the object or body part is performed by means of an optical, preferably monofocal image sensor unit which is connected to a position sensor or comprises the latter, the position of which position sensor is detectable by means of the position detection system. This allows movement of the image sensor unit during the registration, and also at a later stage, relative to the body part or object and relative to the position detection system in order to be able to optically detect the body part or the object from a plurality of locations or from the respectively most expedient location. If the image sensor unit is equipped with a position sensor, the latter can serve as a reference sensor and thus replace or complement a reference sensor arranged on the body part or object. In this case, the position sensor of the image sensor unit supplies information in respect of the location (and alignment) of the image sensor unit.

If the image sensor unit does not comprise a position sensor, there is a need for a reference sensor, which can be detected optically by the image sensor unit, to be precise in such a way that the relative position thereof in relation to the surface to be detected can be established from the optically detected information.

Now, a method for contactless patient registration by means of an optical monofocal image sensor is described. The location (and alignment) of the image sensor unit relative to the patient is preferably monitored. This is brought about by means of a measuring system, preferably the position detection system. Furthermore, the imaging properties of the optical image sensor unit are preferably known in advance.

In accordance with a preferred embodiment variant of the registration method, the image sensor unit is continuously guided during the registration process over the surface to be detected. Here, the relative position of the image sensor unit in relation to the patient (more accurately: in relation to the position detection system)—i.e. the location of the image sensor unit—and the photogrammetrically detected information (i.e., In general) optically detected image data) are recorded.

The photogrammetric detection of the surface is preferably performed using natural illumination, i.e. illumination present in situ.

The location information and the optically detected image data are preferably fed to an iterative algorithm. This algorithm detects objects (edges, lines, circles, etc.) in the optically detected image data (e.g. in individual, images) and is also able to correlate said objects with one another over various individual images. Thus, a list of objects which were recorded by the image sensor unit from different observation directions and observation positions is produced.

Preferably, use is subsequently made of a further algorithm which is able to establish the spatial position of the objects from these data To this end, an object must have been recorded from at least two different observation directions and observation positions. Then, the object position can be established by triangulation.

If a sufficient number of objects and the positions thereof are established, it is possible to perform a conventional surface registration.

Alternatively, the registration method can also be performed as follows using artificial illumination:

In accordance with such an alternative embodiment variant, the image sensor unit is connected (preferably in a rigid manner) to a pattern projector. The relative position between image sensor unit and pattern projector and the imaging properties of the pattern projector are preferably known in advance. Alternatively, the pattern projector can also be connected to a position sensor in such a way that the relative position between image sensor unit and pattern projector can be determined at all times from the position data from the position sensors of the pattern projector and of the image sensor unit. Then, the pattern projector can advantageously be moved independently of the image sensor unit such that the image sensor unit is able in each case to record particularly meaningful individual images with a well evaluable pattern distortion.

The pattern projector can be used to project an artificial structure (a pattern, for example a strip pattern), the dimensions of which are known, onto the target surface in the recording region of the image sensor unit. The pattern projected onto the surface is optically detected by the image sensor unit such that individual images emerge, which show the pattern projected onto the surface with the distortions thereof caused by the form of the surface. The three-dimensional surface can be established in each individual image on the basis of the distortions of the pattern. An overall surface can be determined by combining the three-dimensional partial surfaces of the individual images using the overlapping regions. This overall surface can then be used with the conventional surface registration.

The pattern projector can be configured to project the pattern using infrared light or ultraviolet light. In this case, the image sensor unit is preferably equipped with an infrared-sensitive or ultraviolet-sensitive image sensor. This embodiment variant is advantageous in that the projected pattern is invisible to a surgeon and therefore not able to interfere.

In place of, or in addition to, the pattern projector, provision can also be made for a self-adhesive pattern film. This film is fastened in the target region. As a result of the known patterns on the film, the form of the film, and hence also the surface structure, can be detected.

A further alternative of the registration method provides for the use of a 3-D camera as an image sensor unit, which 3-D camera is able to three-dimensionally record the surface to be detected from the outset. The reconstruction of the surface form from two-dimensional image data, as is required in the method variants described above, then becomes superfluous. Known 3-D cameras record a three-dimensional surface form by virtue of the propagation times of infrared light pulses being measured. This type of recording is also known as a TOF (time of flight) process.

In order to be able to determine possible distortions of an alternating electromagnetic field of the position detection system in all embodiment variants of the registration method, use is made of a plurality of position sensors at different places or of a movable position sensor which is moved during the photogrammetric detection of a surface of the object or body part and the position of which sensor or sensors is likewise detected photogrammetrically. The distortions of the alternating electromagnetic field can then be established from the respective photogrammetrically detected place of the movable position sensor or of the position sensors and from the place determined by the respective position sensor itself by means of the position detection system. Then, it is possible—so to speak—to photogrammetrically measure the alternating electromagnetic field itself.

The image sensor unit may be a small camera, an endoscope or a microscope. If an endoscope is used throughout the whole operation, the described surface identification may be performed continuously. The new information obtained thus can, firstly, be used for correcting the existing patient registration (adaptive patient registration) or, secondly, optionally also additionally be used for updating changes in the patient model caused by the surgical intervention (adaptive patient model).

A continuous registration can advantageously be performed in such a way that there is no longer a need for a reference sensor which is stationary relative to the body part or object. Rather, a position sensor on the respective instrument and/or on a moving image sensor unit would assume the function at a respective time. Such an instrument or such an image sensor unit may, for example, be a microscope that is equipped with a position sensor.

BRIEF DESCRIPTION OF THE DRAWINGS

With aid of the figures, the invention is now intended to be explained in more detail on the basis of an exemplary embodiment. In the figures:

FIG. 2 shows a variant of the device from FIG. 1, in which the position sensor is not arranged on the surface to be detected, but is rather connected to the image sensor unit;

DETAILED DESCRIPTION

Figure 1:
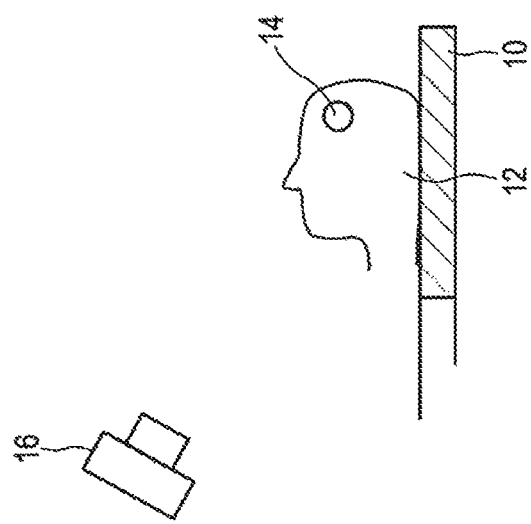
FIG. 1 shows an example of a device for performing a registration method for detecting the position and alignment of an object or body part in relation to a position detection system, wherein the device, in addition to a position detection system, comprises a position sensor arranged on the surface to be detected and an image sensor unit in the form of an optical camera.

FIG. 1 depicts a device for performing a registration method, which device comprises a position detection system 10, a position sensor 14 as a reference sensor, applied on a head 12 of a patient as the body part to the detected, and a camera 16 as an image sensor unit.

An image recorded by the camera 16 for the purposes of registration shows both the body part, namely the head 12 of the patient, and the body part fixed position sensor 16, serving as a reference sensor from one respective perspective. A surface model of the body part 12 can be obtained photogrammetrically from a plurality of recordings of the body part 12. In this photogrammetrically obtained surface model of the body part 12, it is likewise possible to determine the position of the position sensor 16 photogrammetrically. The position of the position sensor 16 is moreover also detected by the position detection system 10, and so the photogrammetrically determined position of the position sensor 14 may be correlated with the position of the position sensor 14 detected by the position detection system 10 such that, by means of the photogrammetrically obtained surface model as well, all further positions on the surface of the body part are known relative to the position sensor 14 and therefore also in the coordinates of the position detection system 10.

In place of a body-part-fixed position sensor 14, as depicted in FIG. 1, provision can also be made for a position sensor 14' on the image sensor unit in the form of the camera 16'. This is depicted in FIG. 2. In this manner, the position detection system 10 in each case detects position and alignment of the image sensor unit (camera) 16 and therefore knows the perspective from which a respective recording, recorded by the image sensor unit 16, originates. This also permits the generation of an accurate surface model from the images recorded by the image sensor unit 16. In this case, the body part to be detected (head of the patient) 12 is preferably connected, as immobile as possible, to the position sensor unit 10. FIG. 2 shows corresponding holders 18 for the head 12 of the patient, which holders are connected to the position detection system 10.

In principle, the recordings recorded by the image sensor unit 16 (camera 16) may be performed in the available light. However, in this case, the extraction of individual geometric and form features of the photographed surface (e.g. the surface of the body part 12) may be difficult in individual cases. In order to obtain more meaningful recordings in this case, provision can advantageously be made for a pattern projector 10, which projects a pattern 22 onto the surface of the body part 12, which pattern is respectively perspectively distorted as a result of the three-dimensional form of the surface of the body part 12. By way of example, pattern projections in the form of strip projections are known for detecting the topography of surfaces.

Figure 3:
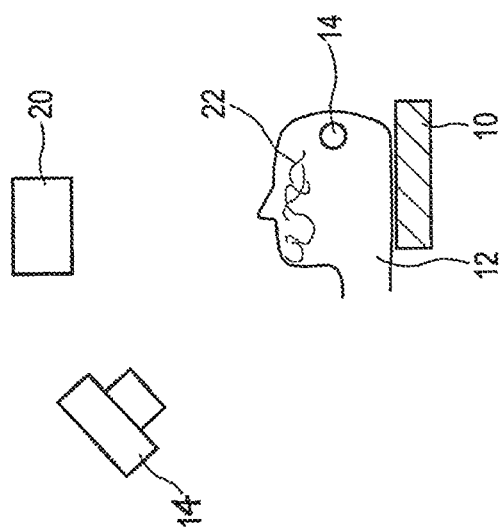
FIG. 3 shows a further variant of the device from FIG. 1, which additionally comprises a pattern projector for projecting a pattern onto the surface to be detected.

FIG. 3 shows such a device with a pattern projector 22.

Figure 4:
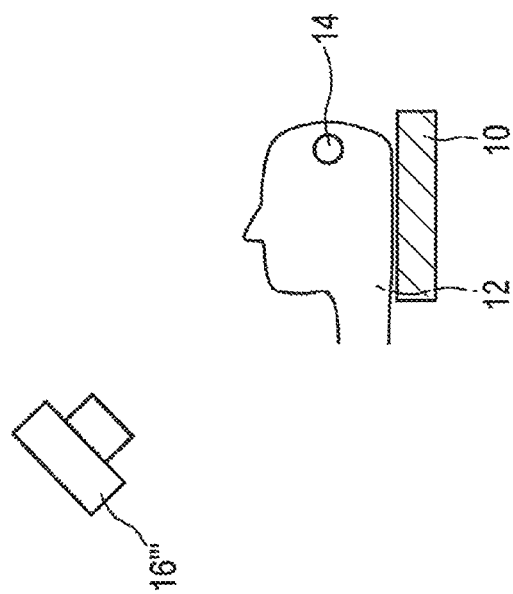
FIG. 4 shows a variant of the device from FIG. 1, in which the image sensor unit is a 3-D camera.

A device, in which each individual recording of the image sensor unit 16''' already supplies information in respect of the three-dimensional surface form of the body part 12, can be realized with an image sensor unit 16''' in the form of a 3-D camera, as is depicted in FIG. 4. Such 3-D cameras 16''' are known per se and record a three-dimensional surface structure, for example according to the time-of-flight system, in which the propagation time or the phase angle of the illumination pulses, which emerge from a corresponding light source of the 3-D camera 16''' and are reflected by the surface of the body part 12, is recorded. Since individual points on the surface of the body part 12 have a different distance from the light source of the image sensor unit 16', and also from the image sensor thereof, this results in pulse propagation times of different length between light source and image sensor. These pulse propagation times (or phase shifts) contain the information relating to the distance between the image sensor unit 16''' and a respective point on the surface of the body part 12.

In all cases, the device is configured in such a way that it supplies a surface model with an accuracy of 1 mm or greater, preferably with an accuracy greater than 0.25 mm. The work space of the device has measurements of the order of several 10 cm in all dimensions, for example between 200 mm×200 mm×200 mm and 500 mm×500 mm×500 mm.

What is claimed is:

1. A registration method for detecting the position and alignment of an object or body part in relation to a position detection system, wherein the method comprises the following steps:
    arranging a reference sensor on the object or body part or on an image sensor unit,
    detecting the position of the reference sensor by a position detection system,
    performing a plurality of image recordings of a surface of the object or body part and of the reference sensor by an optical, monofocal image sensor unit,
    photogrammetrically producing a surface model of the object or body part based on said plurality of recordings,
    determining the position of the reference sensor in the surface model,
    correlating the surface model with a coordinate system of the position detection system by an algorithm and based on the determined position of the reference sensor in the surface model and based on the position of the reference sensor detected by the position detection system.

2. The registration method as claimed in claim 1, characterized in that the optical, monofocal image sensor unit is connected to a position sensor or comprises the latter, the position of which position sensor is detectable by the position detection system.

3. The registration method as claimed in claim 2, characterized in that the image sensor unit is moved during the performing of image recordings of the surface of the object or body part and a respective location and alignment of the image sensor unit is detected by the position sensor on the image sensor unit.

4. The registration method as claimed in claim 3, characterized in that a pattern is projected onto the surface of the object or body part for the purpose of producing the plurality of image recordings of the surface of the object or body part.

5. The registration method as claimed in claim 4, characterized in that the pattern is projected by a pattern projector which is rigidly connected to the image sensor unit.

6. The registration method as claimed in claim 5, characterized in that the pattern is projected by a pattern projector which is rigidly connected to a position sensor.

7. The registration method as claimed in claim 6, characterized in that the pattern is projected using infrared light and the image sensor unit comprises an infrared-sensitive image sensor.

8. The registration method as claimed in claim 7, characterized in that a 3-D camera is used as an image sensor unit.

9. The registration method as claimed in claim 8, characterized in that use is made of a plurality of position sensors at different places or of a movable position sensor which is moved during the producing of the image recordings of the surface of the object or body part and the position of which sensor or sensors is likewise detected photogrammetrically in order to determine distortions of an alternating electromagnetic field of a position detection system.

10. The registration method as claimed in claim 1, characterized in that the at least one image sensor unit is moved during the producing of the image recordings of the surface of the object or body part and a respective location and alignment of the at least one image sensor unit is detected by the position sensor on the at least one image sensor unit.

11. The registration method as claimed in claim 1, characterized in that a pattern is projected onto the surface of the object or body part for the purpose of producing the plurality of image recordings of the surface of the object or body part.

12. The registration method as claimed in claim 11, characterized in that the pattern is projected by a pattern projector which is rigidly connected to the at least one image sensor unit.

13. The registration method as claimed in claim 12, characterized in that the pattern is projected by a pattern projector which is rigidly connected to a position sensor.

14. The registration method as claimed in claim 11, characterized in that the pattern is projected using infrared light and the at least one image sensor unit comprises an infrared-sensitive image sensor.

15. The registration method as claimed in claim 1, characterized in that a 3-D camera is used as an image sensor unit.

16. The registration method as claimed in claim 1, characterized in that use is made of a plurality of position sensors at different places or of a movable position sensor which is moved during the producing of the image recordings of the surface of the object or body part and the position of which sensor or sensors is likewise detected photogrammetrically in order to determine distortions of an alternating electromagnetic field of a position detection system.

17. A device for performing a registration method for detecting the position and alignment of an object or body part in relation to a position detection system, wherein the device comprises:
   a position detection system,
   a reference sensor arranged on the object or body part or on an image sensor unit,
   at least one position sensor, the position and alignment of which is detectable by the position detection system,
   wherein the image sensor unit is an optical, monofocal image sensor unit,
   wherein the position sensor is to be connected to a surface to be detected or is connected to the image sensor unit,
   wherein the image sensor unit is configured to perform a plurality of image recordings of a surface of the object or body part and of the position sensor so as to photogrammetrically produce a surface model of the object or body part based on said plurality of recordings, and so as to determine the position of the position sensor in the surface model, and wherein the position detection system is configured to correlate the surface model with a coordinate system of the position detection system by an algorithm and based on the determined position of the reference sensor in the surface model and based on the position of the reference sensor detected by the position detection system.

18. The device as claimed in claim 17, characterized in that the device additionally comprises a pattern projector which is connected to the at least one image sensor unit and/or a position sensor and/or comprises one of the latter.

19. The device as claimed in claim 17, characterized in that the at least one image sensor unit is a 3-D camera.

* * * * *